United States Patent
Jacobs et al.

(10) Patent No.: US 12,165,780 B2
(45) Date of Patent: Dec. 10, 2024

(54) MULTI-LAYER X-RAY DETECTOR

(71) Applicant: KONINKLIJKE PHILIPS N.V., Eindhoven (NL)

(72) Inventors: Johannes Wilhelmus Maria Jacobs, Bostel (NL); Nishant Singh, Son en Breugel (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 92 days.

(21) Appl. No.: 17/988,800

(22) Filed: Nov. 17, 2022

(65) Prior Publication Data
US 2023/0162880 A1 May 25, 2023

(30) Foreign Application Priority Data
Nov. 23, 2021 (EP) .................................... 21210027

(51) Int. Cl.
*G21K 1/02* (2006.01)
*G01T 1/16* (2006.01)

(52) U.S. Cl.
CPC ............... *G21K 1/025* (2013.01); *G01T 1/16* (2013.01)

(58) Field of Classification Search
CPC .................................. G21K 1/025; G01T 1/16
See application file for complete search history.

(56) References Cited

U.S. PATENT DOCUMENTS

| 8,183,535 | B2 | 5/2012 | Danielsson | |
|---|---|---|---|---|
| 8,917,812 | B2 * | 12/2014 | Ikhlef | A61B 6/4266 378/19 |
| 10,539,683 | B2 * | 1/2020 | De Jong | G01T 1/1611 |
| 2007/0114426 | A1 | 5/2007 | Tkaczyk | |

(Continued)

FOREIGN PATENT DOCUMENTS

| KR | 101320891 B1 | 10/2013 |
|---|---|---|
| KR | 20140046939 A | 4/2014 |

(Continued)

*Primary Examiner* — Hugh Maupin
(74) *Attorney, Agent, or Firm* — Larry Liberchuk (57) ABSTRACT

A multi-layer X-ray detector comprises a first X-ray converter, a first sensor, a second X-ray converter, a second sensor, and an internal anti-scatter device. The first sensor is located at a first sensor layer and is configured to detect radiation emitted from the first X-ray converter. The second sensor is located at a second sensor layer and is configured to detect radiation emitted from the second X-ray converter. The first X-ray converter and the first sensor form a first detector pair, and the second X-ray converter and the second sensor form a second detector pair. The internal anti-scatter device comprises a plurality of X-ray absorbing septa walls and is located between the first detector pair and the second detector pair. No structure of the internal anti-scatter device is located within either layer of the first detector pair, and no structure of the anti-scatter device is located within either layer of the second detector pair. The plurality of septa walls comprises a plurality of first septa walls substantially parallel to each other, and wherein a spacing between the first (Continued)

septa walls in a first direction is equal to an integer multiple n of detector pixel pitch of the first sensor and/or of the second sensor in the first direction, wherein n=2, 3, 4, . . . N.

9 Claims, 4 Drawing Sheets

(56) References Cited

U.S. PATENT DOCUMENTS

| | | | |
|---|---|---|---|
| 2010/0127180 A1* | 5/2010 | Lifshitz | G01T 1/2002 |
| | | | 438/73 |
| 2010/0204942 A1 | 8/2010 | Danielsson | |
| 2012/0097858 A1 | 4/2012 | Morf | |
| 2017/0090039 A1 | 3/2017 | Hoffman | |
| 2017/0269238 A1 | 9/2017 | Danielsson | |
| 2019/0374182 A1 | 12/2019 | Karim | |
| 2020/0268330 A1* | 8/2020 | Altunbas | A61B 6/4035 |
| 2021/0244374 A1* | 8/2021 | Zhao | A61B 6/482 |

FOREIGN PATENT DOCUMENTS

| | | |
|---|---|---|
| WO | WO2017007326 A1 | 1/2017 |
| WO | WO2018122213 A1 | 7/2018 |
| WO | WO2019232650 A1 | 12/2019 |

* cited by examiner

MULTI-LAYER X-RAY DETECTOR

FIELD OF THE INVENTION

The present invention relates to multi-layer X-ray detector.

BACKGROUND OF THE INVENTION

Multi-layer radiation X-ray detectors suffer from (back) scatter of X-rays between the detection layers, which deteriorates detector performance. In dual-energy X-ray imaging based on one-shot exposure of a dual-layer detector, the number of scattered X-rays from the top scintillator layer into the bottom scintillator layer can be so large that the X-ray image acquired by the bottom sensor is dominated by scatter instead of the primary signal. This reduces spectral differentiation capability of the detector.

In US2007/0114426 A1 an X-ray detector system with improved spatial resolution for a computed tomography system is provided. The detector system may include pairs of first and second detector arrays and, with each array containing detector elements of a different design. In one embodiment, the first array may comprise a first, relatively thin and continuous (i.e., monolithic) scintillation layer with an array of individual diodes positioned to receive light generated within the scintillation layer. The second array may comprise a second, relatively thick scintillation layer formed of separate scintillator elements.

US2019/0374182 A1 describes a method and apparatus for determining virtual outputs for a multi-energy x-ray apparatus. Based on the application that the x-ray apparatus is being used for, a general algorithm can be determined or selected. Inputs received from the x-ray apparatus can be substituted into the general algorithm to generate a virtual output algorithm for the x-ray apparatus. Virtual outputs can then be calculated using the virtual output algorithm.

In US2012/0097858 A1 a multi-layered mega-voltage digital imager is disclosed. In one embodiment, the radiation to particle conversion and particle to electricity conversion is paired as a modular entity. The entity is replicated on top of each other as a layered unit to build an imager with increased resolution and efficiency. Due to this paired replication, sub-images from each replicated pair may be selectively combined and processed to enhance the quality of the image.

WO2017/007326 A1 describes a dual mode radiation detector comprising an x-ray detector layer to convert incident x-ray radiation into x-ray electrical data, said x-ray detector forming an incident face of said dual mode radiation detector, a collimator disposed below the x-ray detector layer, and a gamma photon detector layer disposed below the collimator to convert incident gamma photons into gamma photon electrical data.

Besides a good spectral differentiation, it is important to get a high enough primary transmission signal to the pixels of multi-layer radiation X-ray detectors. A lower signal-to-noise ratio might be increased again by increasing x-ray dose, but this is unacceptable in the current practice of medical x-ray imaging. There is a need to resolve this issue.

SUMMARY OF THE INVENTION

It would be advantageous to have an improved multi-layer X-ray detector. The invention is defined by the independent claim, wherein further embodiments are defined by the dependent claims.

In a first aspect, there is provided a multi-layer X-ray detector, comprising:
 a first X-ray converter;
 a first sensor;
 a second X-ray converter;
 a second sensor; and an internal anti-scatter device.

The first X-ray converter is located at a first X-ray conversion layer. The first sensor is located at a first sensor layer. The second X-ray converter is located at a second X-ray conversion layer. The second sensor is located at a second sensor layer. The first X-ray converter and the first sensor form a first detector pair, and the first sensor is configured to detect radiation emitted from the first X-ray converter generated from the conversion of X-rays in the first X-ray converter. The second X-ray converter and the second sensor form a second detector pair, and the second sensor is configured to detect radiation emitted from the second X-ray converter generated from the conversion of X-rays in the second X-ray converter. The internal anti-scatter device comprises a plurality of X-ray absorbing septa walls. The internal anti-scatter device is located between the first detector pair and the second detector pair. No structure of the internal anti-scatter device is located within either layer of the first detector pair, and no structure of the anti-scatter device is located within either layer of the second detector pair. The plurality of septa walls comprises a plurality of first septa walls substantially parallel one to another-thus they are substantially parallel to each other. A spacing between the first septa walls in a first direction is equal to an integer multiple n of detector pixel pitch of the first sensor and/or of the second sensor in the first direction, wherein n=2, 3, 4, . . . . N.

In this manner forward-scatter and back-scatter within a detector between the detection layers can be mitigated that would otherwise deteriorate detector performance. Thus, spectral differentiation in dual-energy detectors can be improved though the integration of an anti-scatter device or anti-scatter grid within the detector structure that does not have any structure in a plane of detection layers of the device. Also, the fill factor of X-ray conversion can be kept at 100%. With the current invention, back-scatter can be mitigated with the grid while at the same time negative impact of the grid walls on primary transmission may be reduced. This is particularly advantageous for medical X-ray applications that require high resolution/small pixels and limited X-ray dose to the patients.

In an example, the first septa walls are aligned with junctions between adjacent pixels of the first sensor and/or of the second sensor in the first direction. Aligning the septa walls with the junctions or gaps between adjacent pixels is advantageous to further limit negative impact of the septa walls on primary transmission.

In an example, the first sensor layer is adjacent to the first X-ray conversion layer; and wherein the second sensor layer is adjacent to the second X-ray conversion layer.

In an example, the first sensor layer is adjacent to the internal anti-scatter device.

In an example, the first X-ray conversion layer is adjacent to the internal anti-scatter device.

In an example, the second sensor layer is adjacent to the internal anti-scatter device.

In an example, the second X-ray conversion layer is adjacent to the internal anti-scatter device.

In an example, the plurality of septa walls comprises a plurality of second septa walls substantially parallel one to another. A spacing between the second septa walls in a second direction is equal to an integer multiple n of detector pixel pitch of the first sensor and/or of the second sensor in the second direction, wherein n=1, 2, 3, 4, . . . . N, and wherein the second direction is at an angle to the first direction. Such a multi-layer detector comprising an internal two-dimensional anti-scatter device may be particularly useful for applications such as Computed Tomography.

In an example, the second septa walls are aligned with junctions between adjacent pixels of the first sensor and/or of the second sensor in the first direction.

In an example, the detector pixel pitch of the first sensor and/or of the second sensor in the first direction is less than or equal to 200 µm. As mentioned above, the invention may be particularly advantageous to limit negative impact of septa walls on primary transmission for small pixel sizes, especially if the dose is limited.

In an example, the detector pixel pitch of the first sensor and/or of the second sensor in the first direction is 175 µm, 150 µm, 125 µm, 100 µm, 75 µm, 50 µm, 25 µm, 10 µm, or 5 µm.

In an example, the detector pixel pitch of the first sensor and/or of the second sensor in the second direction is less than or equal to 200 µm.

In an example, the detector pixel pitch of the first sensor and/or of the second sensor in the second direction is 175 µm, 150 µm, 125 µm, 100 µm, 75 µm, 50 µm, 25 µm, 10 µm, or 5 µm.

In an example, the detector is configured such that the internal anti-scatter device can be removed from between the first detector pair and the second detector pair.

In this way, the detector can be adapted to the thickness of the patient or part of the patient. Thus, for thin patients, such as children, and for thin body parts, where there is little X-ray scattering the anti-scatter device can be removed to improve image quality. However, for thicker patients, where there is X-ray scattering, the anti-scatter device (ASD) can be placed within the detector to reduce scattering within the detector that would otherwise deteriorate detector performance.

In an example, the plurality of X-ray absorbing septa walls comprise at least one high-Z material. Materials with high atomic number, so called high-Z materials, may be particularly efficient in reducing scatter effects in a multi-layer detector with an integrated anti-scatter device.

The above aspect and examples will become apparent from and be elucidated with reference to the embodiments described hereinafter.

BRIEF DESCRIPTION OF THE DRAWINGS

Exemplary embodiments will be described in the following with reference to the following drawing.

DETAILED DESCRIPTION OF EMBODIMENTS

Figure 1:
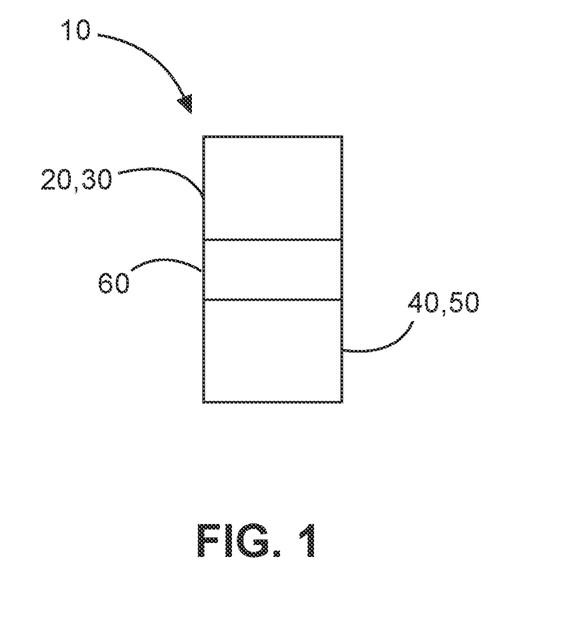
FIG. 1 shows a schematic representation of an example of a multi-layer X-ray detector.

FIG. 1 shows an example of a multi-layer X-ray detector 10. The detector 10 comprises a first X-ray converter 20, a first sensor 30, a second X-ray converter 40, a second sensor 50, and an internal anti-scatter device 60. The first X-ray converter is located at a first X-ray conversion layer. The first sensor is located at a first sensor layer. The second X-ray converter is located at a second X-ray conversion layer. The second sensor is located at a second sensor layer. The first X-ray converter and the first sensor form a first detector pair, and the first sensor is configured to detect radiation emitted from the first X-ray converter generated from the conversion of X-rays in the first X-ray converter. The second X-ray converter and the second sensor form a second detector pair, and the second sensor is configured to detect radiation emitted from the second X-ray converter generated from the conversion of X-rays in the second X-ray converter. The internal anti-scatter device comprises a plurality of X-ray absorbing septa walls. The internal anti-scatter device is located between the first detector pair and the second detector pair. No structure of the internal anti-scatter device is located within either layer of the first detector pair and no structure of the anti-scatter device is located within either layer of the second detector pair.

In an example, the plurality of X-ray absorbing septa walls comprise at least one high-Z material.

In an example, the internal anti-scatter device can be a 1D device with a plurality of X-ray absorbing septa walls that are substantially parallel to one another.

In an example, the internal anti-scatter device can be a 2D device with a plurality of first X-ray absorbing septa walls that are substantially parallel to one another in a first direction and a plurality of second X-ray absorbing septa walls that are substantially parallel to one another in a second direction angled to the first direction. The second direction can be orthogonal to the first direction, suitable for square or rectangular pixels, or could be angled at 60 degrees, suitable for hexagonal pixels. Other angles are possible.

According to an example, the first sensor layer is adjacent to the first X-ray conversion layer; and the second sensor layer is adjacent to the second X-ray conversion layer.

According to an example, the first sensor layer is adjacent to the internal anti-scatter device.

According to an example, the first X-ray conversion layer is adjacent to the internal anti-scatter device.

According to an example, the second sensor layer is adjacent to the internal anti-scatter device.

According to an example, the second X-ray conversion layer is adjacent to the internal anti-scatter device.

The plurality of septa walls comprises a plurality of first septa walls substantially parallel one to another. A spacing between the first septa walls in a first direction is equal to an integer multiple n of detector pitch of the first sensor and/or of the second sensor in the first direction, wherein n=, 2, 3, 4, . . . . N.

According to an example, the first septa walls are aligned with the junctions between adjacent pixels.

According to an example, the plurality of septa walls comprises a plurality of second septa walls substantially parallel one to another. A spacing between the second septa walls in a second direction is equal to an integer multiple n of detector pitch of the first sensor and/or of the second sensor in the second direction, wherein n=1, 2, 3, 4, . . . . N, and wherein the second direction is at an angle to the first direction.

In an example, the second direction is orthogonal to the first direction.

According to an example, the second septa walls are aligned with the junctions between adjacent pixels.

According to an example, the detector pitch of the first sensor and/or of the second sensor in the first direction is less than or equal to 200 μm.

According to an example, the detector pitch of the first sensor and/or of the second sensor in the first direction is 175 μm, 150 μm, 125 μm, 100 μm, 75 μm, 50 μm, 25 μm, 10 μm, or 5 μm.

According to an example, the detector pitch of the first sensor and/or of the second sensor in the second direction is less than or equal to 200 μm.

According to an example, the detector pitch of the first sensor and/or of the second sensor in the second direction is 175 μm, 150 μm, 125 μm, 100 μm, 75 μm, 50 μm, 25 μm, 10 μm, or 5 μm.

According to an example, the detector is configured such that the internal anti-scatter device can be removed from between the first detector pair and the second detector pair.

Figure 9:
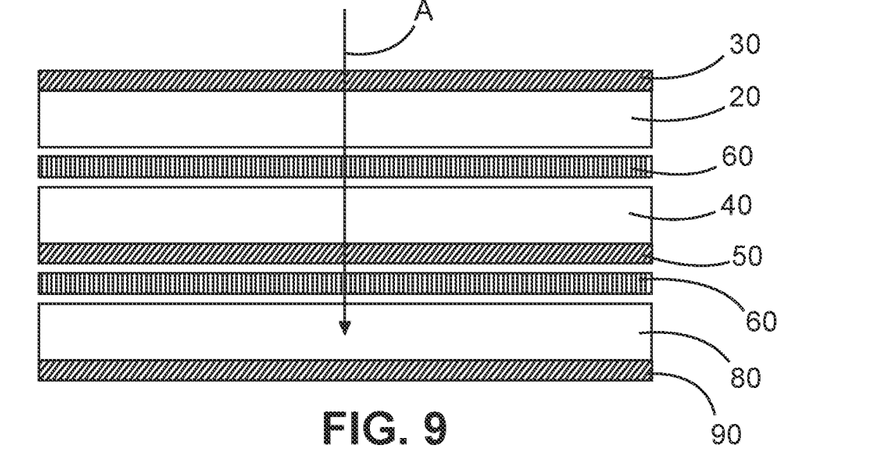
FIG. 9 shows a schematic representation of an example of a multi-layer X-ray detector with an internal anti-scatter device.

In an example, shown for example in FIG. 9, the multi-layer X-ray detector 10 comprises: a third X-ray converter 80; a third sensor 90; and a further internal anti-scatter device 60. The third X-ray converter is located at a third X-ray conversion layer. The third sensor is located at a third sensor layer. The third X-ray converter and the third sensor form a third detector pair. The third sensor is configured to detect radiation emitted from the third X-ray converter generated from the conversion of X-rays in the third X-ray converter. The further internal anti-scatter device comprises a plurality of X-ray absorbing septa walls. The further internal anti-scatter device is located between the second detector pair and the third detector pair. No structure of the further internal anti-scatter device is located within either layer of the second detector pair and no structure of the further internal anti-scatter device is located within either layer of the third detector pair.

In an example, the plurality of X-ray absorbing septa walls of the further internal anti-scatter device comprise at least one high-Z material.

In an example, the further internal anti-scatter device can be a 1D device with a plurality of X-ray absorbing septa walls that are substantially parallel to one another.

In an example, the further internal anti-scatter device can be a 2D device with a plurality of first X-ray absorbing septa walls that are substantially parallel to one another in a first direction and a plurality of second X-ray absorbing septa walls that are substantially parallel to one another in a second direction angled to the first direction. The second direction can be orthogonal to the first direction, suitable for square or rectangular pixels, or could be angled at 60 degrees, suitable for hexagonal pixels. Other angles are possible.

In an example, the third sensor layer is adjacent to the third X-ray conversion layer.

In an example, the second sensor layer is adjacent to the further internal anti-scatter device.

In an example, the third X-ray conversion layer is adjacent to the further internal anti-scatter device.

In an example, the plurality of septa walls of the further internal anti-scatter device comprises a plurality of first septa walls substantially parallel one to another. A spacing between the first septa walls in a first direction is equal to an integer multiple n of detector pitch of the second sensor and/or of the third sensor in the first direction, wherein n=1, 2, 3, 4, . . . N.

In an example, the first septa walls of the further internal anti-scatter grid are aligned with the junctions between adjacent pixels.

In an example, the plurality of septa walls of the further internal anti-scatter grid comprises a plurality of second septa walls substantially parallel one to another. A spacing between the second septa walls in a second direction is equal to an integer multiple n of detector pitch of the second sensor and/or of the third sensor in the second direction, wherein n=1, 2, 3, 4, . . . . N, and wherein the second direction is at an angle to the first direction.

In an example, the second direction is orthogonal to the first direction.

In an example, the second septa walls are aligned with the junctions between adjacent pixels.

In an example, the detector pitch of the third sensor in the first direction is less than or equal to 200 μm.

In an example, the detector pitch of the third sensor in the first direction is 175 μm, 150 μm, 125 μm, 100 μm, 75 μm, 50 μm, 25 μm, 10 μm, or 5 μm.

In an example, the detector pitch of the third sensor in the second direction is less than or equal to 200 μm.

In an example, the detector pitch of the third sensor in the second direction is 175 μm, 150 μm, 125 μm, 100 μm, 75 μm, 50 μm, 25 μm, 10 μm, or 5 μm.

In an example, the detector is configured such that the further internal anti-scatter device can be removed from between the first detector pair and the second detector pair.

Figure 10:
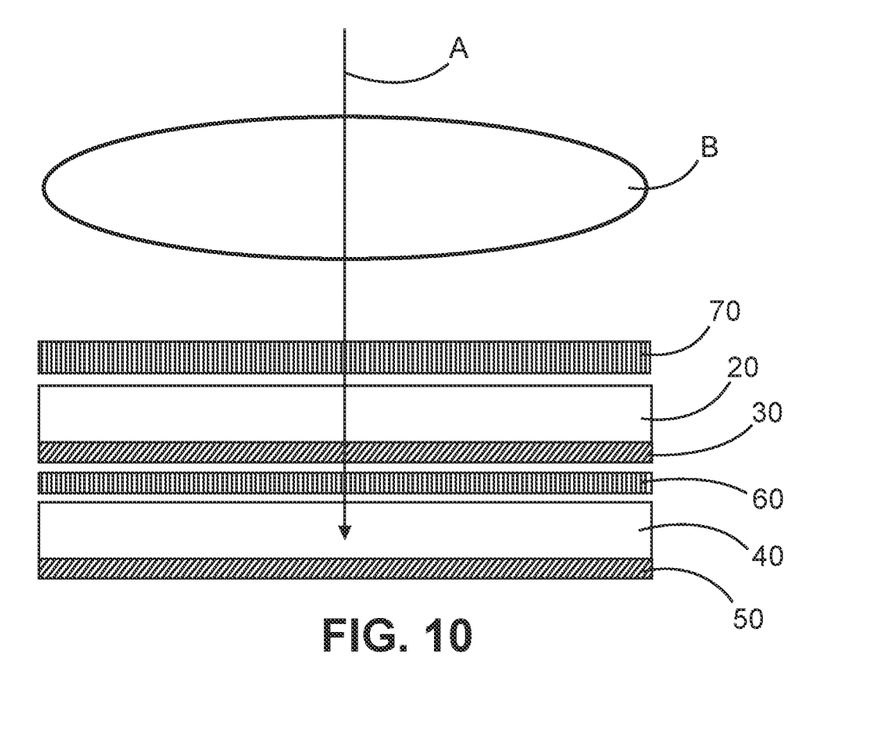
FIG. 10 shows a schematic representation of an example of a multi-layer X-ray detector with an internal anti-scatter device and an external anti-scatter device in the form of an anti-scatter grid.

In an example, an external anti-scatter device 70 is located adjacent to the first detector pair on the opposite side of the first detector pair to the internal anti-scatter grid 60. The external anti-scatter device comprises a plurality of X-ray absorbing septa walls. This is shown in FIG. 10.

In an example, the plurality of X-ray absorbing septa walls comprise at least one high-Z material.

In an example, the external anti-scatter device can be a 1D device with a plurality of X-ray absorbing septa walls that are substantially parallel to one another.

In an example, the external anti-scatter device can be a 2D device with a plurality of first X-ray absorbing septa walls that are substantially parallel to one another in a first direction and a plurality of second X-ray absorbing septa walls that are substantially parallel to one another in a second direction angled to the first direction. The second direction can be orthogonal to the first direction, or could be angled at 60 degrees. Other angles are possible.

In an example, the plurality of septa walls of the external anti-scatter grid are aligned with the plurality of septa walls of the anti-scatter grid.

Current resolutions of anti-scatter grids used in medical X-ray imaging are commonly in the range of 25 to 80 lp/cm (line pairs per centimeter), which corresponds to a grid pitch in the range 125-400 µm. In general, the primary X-ray transmission of the grid reduces when the grid resolution, i.e. the number of septa walls per unit length, increases. This is caused by the fact that septa walls not only absorb scattered X-rays but also primary X-rays. Accordingly, the so-called "image improvement factor" or Q-factor of the grid, which is proportional to the square of its primary X-ray transmission, will drop drastically at higher grid resolutions. Furthermore, from grid manufacturing point of view, it becomes increasingly difficult to produce grids with resolutions above 80 lp/cm and simultaneously having sufficient quality and uniformity across the complete grid surface area.

At the same time, for x-ray detectors there is a clear trend to reduce the pixel pitch (pixel pitch≤100 µm), which is driven by the clinical need for higher spatial resolution in many x-ray imaging applications.

A combination of a high-resolution x-ray detector with a standard anti-scatter device will reduce the number of X-ray quanta reaching the detector, and thereby its signal. This would lead to a lower x-ray detective quantum efficiency (DQE), i.e. X-ray images with increased noise levels. This lower signal-to-noise ratio might be increased again by increasing x-ray dose, but this is unacceptable in the current practice of medical X-ray imaging.

The current invention proposes to combine the high-resolution X-ray detector with an anti-scatter device with a grid pitch equal to an integer multiple of the detector pixel pitch and optionally by aligning the grid septa walls accurately with the inactive areas between detector pixels.

Thus, the problem of a reduction in spectral differentiation and/or reduced DQE may be solved by integrating an internal anti-scatter device (ASD), or indeed more than one internal anti-scatter device, such as an anti-scatter grid (ASG), inside the X-ray detector.

In this way, both high-resolution capabilities of the x-ray detector and a high Q-factor of the grid, i.e. excellent anti-scatter performance, can be maintained. Furthermore, during x-ray image acquisition one can optionally choose to do pixel binning, which can have advantages in specific imaging applications. For example, with an integrated 2D ASG, in the case of pixel binning all pixels can be chosen to be identical (e.g. 3×3 pixels, n=3) which will reduce aliasing effects and simplify the required image processing to reduce image artefacts caused by grid septa walls. Alternatively, one can choose to do no pixel binning (e.g. 1×1 pixel, n=3) which will simplify x-ray scatter correction models as there are only a few types of detector pixels.

The multi-layer X-ray detector will now be described in specific detail, where reference is made to FIGS. 2-10.

Figure 2:
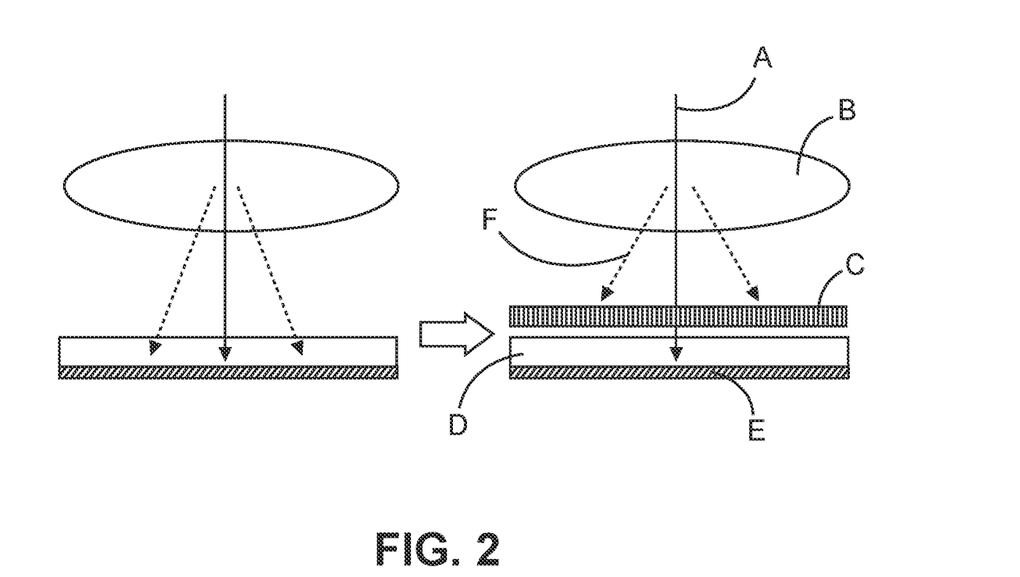
FIG. 2 shows a schematic representation of an example of an external ant-scatter device, in the form of an anti-scatter grid, positioned between the object and X-ray detector.

When scattered X-rays from a patient are collected by an imaging detector, they do not provide any additional information about the anatomy of the patient, but they degrade image quality by reducing contrast in the image. Hence an external anti-scatter grid (ASG) has been used for many decades in medical X-ray and CT imaging to absorb scattered X-rays and thereby improve image quality. This is shown schematically in FIG. 2 that shows an object and detector on the left, and where on the right an external ASG has been placed between the object and the X-ray detector. In FIG. 2 a primary X-ray is represented by "A", Object is represented by "B", external ASG is represented by "C", X-ray conversion layer is represented by "D", sensor is represented by "E", and Scattered X-ray is represented by "F".

Figure 3:
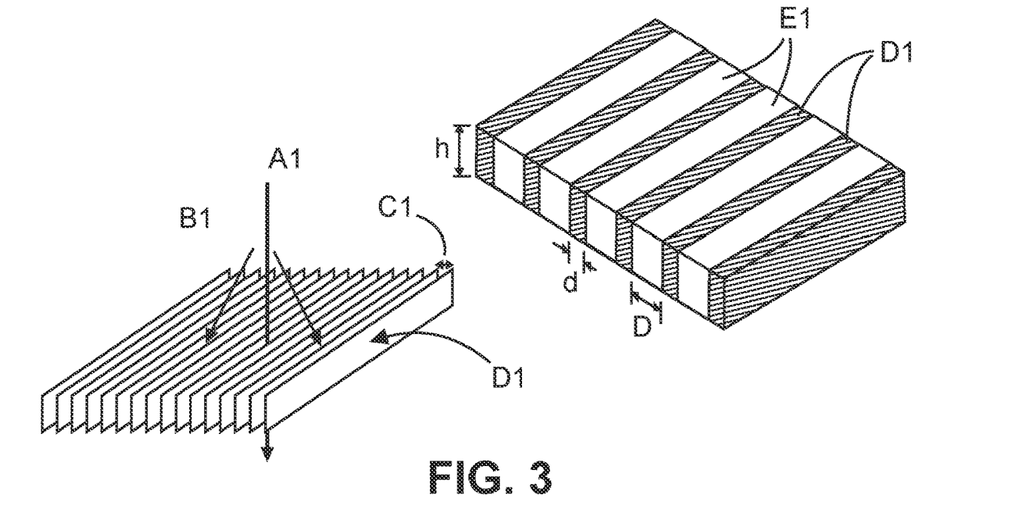
FIG. 3 shows a schematic representation of an example of an anti-scatter device in the form of a 1D anti-scatter grid.
Figure 4:
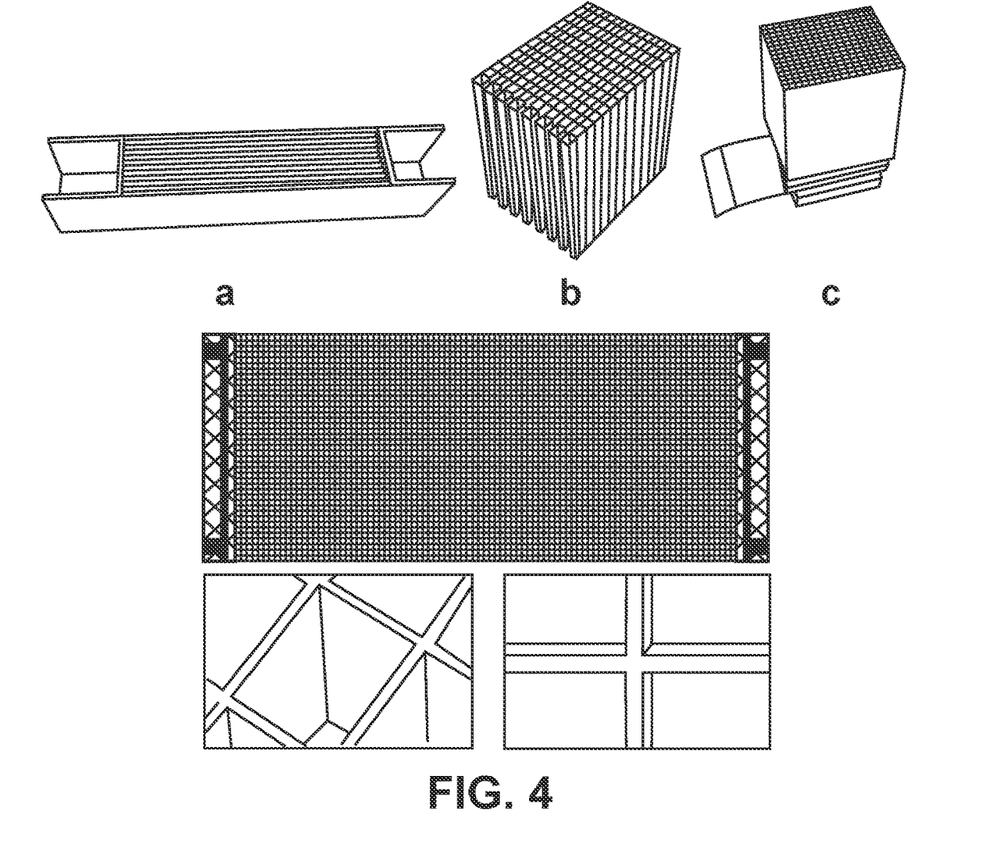
FIG. 4 shows a schematic representation of examples of anti-scatter devices in the form of 2D anti-scatter grids.

For illustration, a large-area 1D ASG used in X-ray systems is shown in FIG. 3, and examples of 2D ASGs used in CT systems are shown in FIG. 4.

Multi-layer radiation detectors enable spectral imaging (e.g. dual-energy x-ray imaging, megavolt spectral imaging) and/or increased detector performance (e.g. higher DQE). However, a large portion of X-rays entering a standard multi-layer detector are scattered by the first detection layer and are captured by the second detection layer. This degrades detector performance, since scattered X-rays do not contain useful information. These scattered X-rays cause undesired image signals in the second detection layer, which add up to image signals of primary X-rays captured by the second detection layer. Furthermore, scattered X-rays are partly scattered back from the second detection layer into the first detection layer and thereby deteriorate image signals of primary X-rays captured by the first detection layer. Finally, K-fluorescence signals from the first detection layer may enter into the second detection layer. Similar (back) scatter and K-fluorescence phenomena occur in all successive layers of a standard multi-layer detector. Consequently, image quality parameters (MTF, DQE, contrast-to-noise ratio, signal-to-noise) for each detection layer are reduced to a certain extent, depending on factors such as exposure conditions, detector configuration, clinical application, etc. In spectral X-ray imaging this causes a severe reduction in spectral differentiation capability of the detection layers, which generates various shortcomings, such as inaccurate material decompositions, low-quality virtual monochromatic images, and CBCT image reconstruction artefacts. In particular, in dual-energy X-ray imaging based on one-shot exposure of a dual-layer detector, the number of scattered X-rays from the top scintillator layer into the bottom scintillator layer can be so large that it dominates the X-ray signal acquired by the bottom sensor.

It has been established that an anti-scatter device, that is located internally within the X-ray detector and located spatially separately to the first and second detection layers, addresses the above problems.

Figure 5:
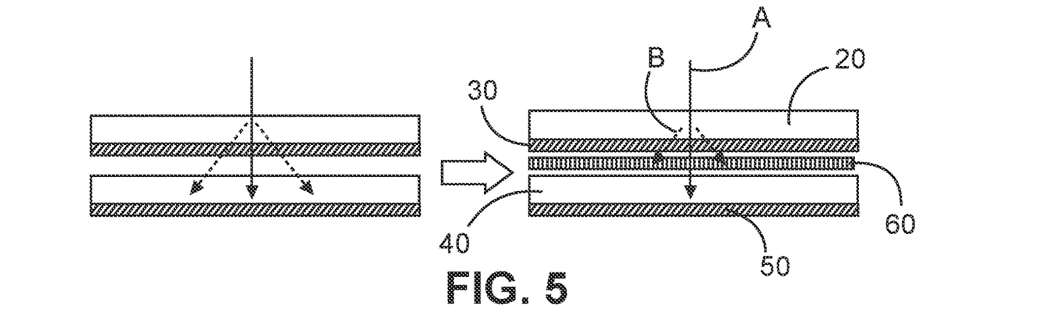
FIG. 5 shows a schematic representation of an example of a multi-layer X-ray detector with an internal anti-scatter device.

It has been established that (back) scatter between detection layers in a multi-layer radiation detector can be reduced, and thereby detector performance increased, by implementation of an ASD between one or more detection layers. This is shown schematically in FIG. 5 for an ASD inserted between the two detection layers of a dual-layer detector. This integrated ASD may physically be very similar to a standard 1D ASG or 2D ASG, but can have a spacing between septa walls that is much smaller than ASGs used for CT detectors. In FIG. 5 a primary X-ray is represented by "A", a scattered X-ray is represented by "B", X-ray conversion layer 1 is represented by "20", sensor 1 by "30", X-ray conversion layer 2 by "40", sensor 2 by "50", and internal ASD by "60". The ASD can be integrated but can also be removed, but in both cases when present it is located internally within the X-ray detector structure and separated from detection layers.

Figure 6:
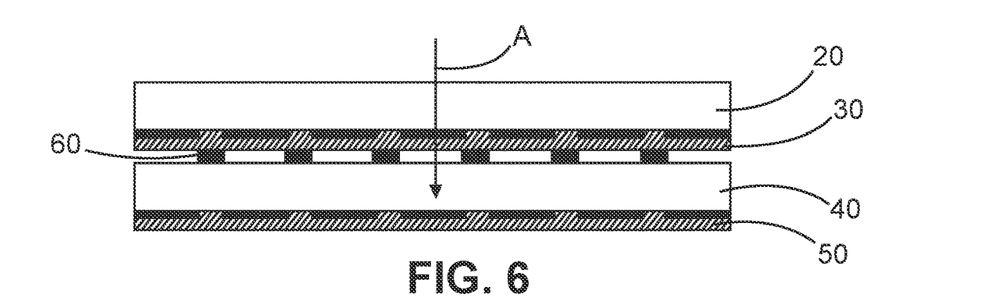
FIG. 6 shows a schematic representation of an example of a multi-layer X-ray detector with an internal anti-scatter device.

The ASD can be in the form of a patterned layer of high-Z material, such as a (stacked) tungsten foil, with pixel openings aligned with sensor pixels, as schematically shown in FIG. 6. In FIG. 6 a primary X-ray is represented by "A", X-ray conversion layer 1 is represented by "20", sensor 1 by "30", X-ray conversion layer 2 by "40", sensor 2 by "50", and internal ASD by "60". The ASD can again be integrated but can also be removed.

Figure 7:
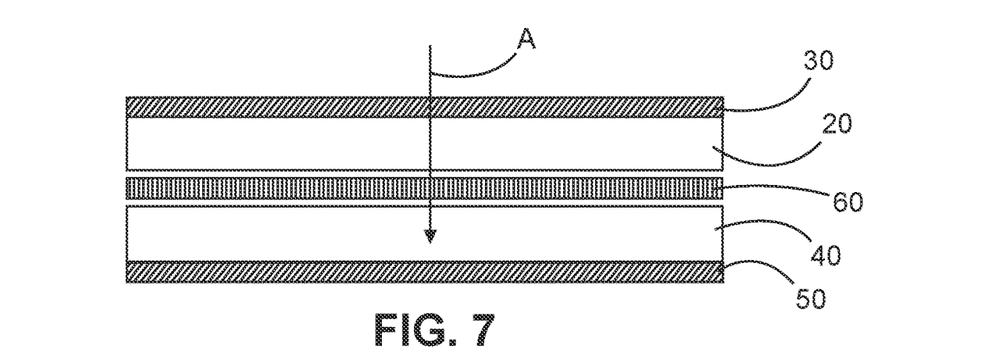
FIG. 7 shows a schematic representation of an example of a multi-layer X-ray detector with an internal anti-scatter device.
Figure 8:
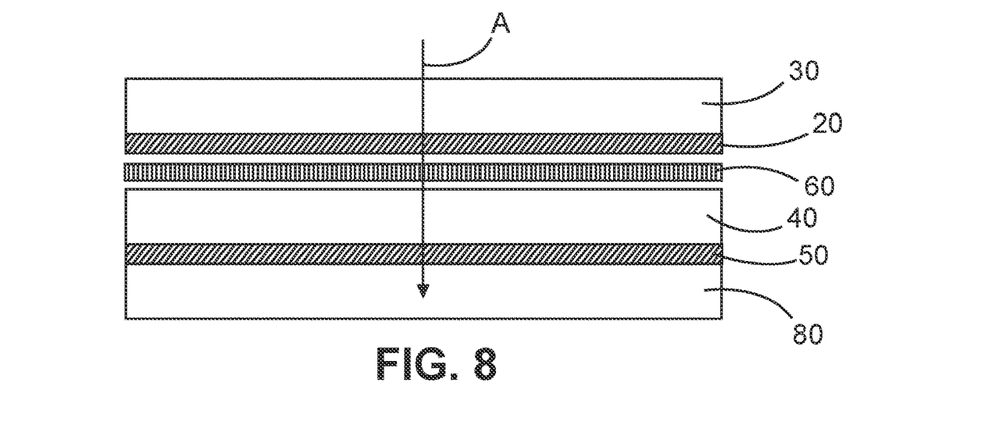
FIG. 8 shows a schematic representation of an example of a multi-layer X-ray detector with an internal anti-scatter device.

For further illustration, FIGS. 7, 8, and 9 show examples of how an internal ASD can be integrated in three different multi-layer detector designs.

FIG. 7 shows a symmetric sandwich of two detection layers on both sides of an ASD. In FIG. 7 a primary X-ray is represented by "A", X-ray conversion layer 1 is represented by "20", sensor 1 by "30", X-ray conversion layer 2 by "40", sensor 2 by "50", and internal ASD by "60". The ASD can again be integrated but can also be removed.

FIG. 8 shows a foil-based triple-layer dual-sensor detector with the bottom sensor 2 (50) receiving scintillator light from the top and bottom sides. In FIG. 8 a primary X-ray is represented by "A", X-ray conversion layer 1 is represented by "20", sensor 1 by "30", X-ray conversion layer 2 by "40", sensor 2 by "50", X-ray conversion layer 3 by "80", and internal ASD by "60". The ASD can again be integrated but can also be removed.

FIG. 9 shows a triple-layer detector with two ASDs. In FIG. 9 a primary X-ray is represented by "A", X-ray conversion layer 1 is represented by "20", sensor 1 by "30", X-ray conversion layer 2 by "40", sensor 2 by "50", X-ray conversion layer 3 by "80", sensor 3 by "90", and the two internal ASDs by "60".

As explained in the initial discussion, an external ASG (or ASD) can provide benefits along with an internal ASD newly developed and described here. FIG. 10 shows an example a multi-layer detector that makes combined use of an external ASG and an internal ASD to maximize detection performance. Positional alignment features between the internal ASD and the external ASG and/or pixel structures of sensor 1 can be added in order to maximize transmission of primary X-rays to sensor 2. In FIG. 10 a primary X-ray is represented by "A", object by "B", X-ray conversion layer 1 is represented by "20", sensor 1 by "30", X-ray conversion layer 2 by "40", sensor 2 by "50", internal ASD by "60", and external ASG by "70".

It is to be noted that the pixel pitch of the X-ray detector can be of the order of 5 μm to 200 μm and the septa wall spacing of the internal ASD, equal to d+D as shown in FIG. 3 which can be 1D or 2D, can be equal to 5 μm to 200 μm.

Many options exist to configure an optimal integrated ASD for a specific multi-layer radiation detector and its intended main imaging application(s).

Options:
Imaging applications include X-ray, CT, CBCT NDT, radiotherapy systems and EPID (MV radiation).
Detector can be a large-area device (e.g. X-ray detector) or a small module (e.g. CT tile)
Detector consists of multiple layers of indirect and/or direct x-ray conversion materials, each layer is coupled to a pixelated image sensor
X-ray image acquisition is based on energy integrating or photon counting
Multiple ASD's can be used when the detector has 3 or more sensor layers.
ASD is a focused 1D or 2D ASG consisting of multiple septa walls separated by interspacer material
Septa material can consist of high-Z elements (Pb, W, Bi, Ta, . . . )
Interspacer materials consists of air or x-ray absorbing (filter) material (carbon, silicon, glass, polymer, aluminum, copper, tin, . . . )
Examples: lead-fiber 1D ASG, lead-aluminum or lead-carbon 1D ASG, DMLS tungsten 2D ASG, RIE-patterned silicon grooves filled with CsI,
ASD is a patterned layer of high-Z material with pixel openings aligned with sensor pixels.
High-Z layer can be processed together with x-ray conversion material or sensor substrate.
Example: thick (stacked) metal foil bonded directly to x-ray conversion material or to sensor substrate, or can be free-standing.
Example: thin tungsten foil with array of square pixel openings separated by septa walls.
ASD may also act as x-ray absorbing filter. Therefore, the septa walls may also consist of low-Z elements, such as tin, copper or aluminum.
ASD septa walls are aligned and (partly) overlap with septa walls of external ASG to maximize transmission of primary x-rays (most relevant for CT).
ASD septa walls are aligned and (partly) overlap with inactive regions between sensor pixels to maximize transmission of primary x-rays (most relevant for CT).
ASD may be flat or curved.
ASD may be removed from multi-layer detector (and inserted back again)

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. Any reference signs in the claims should not be construed as limiting the scope.

What is claimed is:
1. A multi-layer X-ray detector, comprising:
a first X-ray converter;
a first sensor located at a first sensor layer and configured to detect radiation emitted from the first X-ray converter;
a second X-ray converter;
a second sensor located at a second sensor layer and configured to detect radiation emitted from the second X-ray converter, wherein the first X-ray converter and the first sensor form a first detector pair, and the second X-ray converter and the second sensor form a second detector pair; and
an internal anti-scatter device located between the first detector pair and the second detector pair and includes a plurality of X-ray absorbing septa walls, wherein no structure of the internal anti-scatter device is located within either layer of the first detector pair, and no structure of the internal anti-scatter device is located within either layer of the second detector pair; and
wherein the detector pixel pitch of the first sensor and/or of the second sensor in the first direction is less than or equal to 200 μm.

2. The multi-layer detector according to claim 1, wherein the first septa walls are aligned with junctions between adjacent pixels of the first sensor and/or of the second sensor in the first direction.

3. The multi-layer detector according to claim 1, wherein the plurality of septa walls comprises a plurality of second septa walls substantially parallel to each other, wherein a spacing between the second septa walls in a second direction is equal to an integer multiple n of detector pixel pitch of the first sensor and/or of the second sensor in the second direction, wherein n=1, 2, 3, 4, . . . N, and wherein the second direction is at an angle to the first direction.

4. The multi-layer detector according to claim 3, wherein the second septa walls are aligned with junctions between adjacent pixels of the first sensor and/or of the second sensor in the first direction.

5. The multi-layer detector according to claim 1, wherein the detector pixel pitch of the first sensor and/or of the second sensor in the first direction is one of: 175 μm, 150 μm, 125 μm, 100 μm, 75 μm, 50 μm, 25 μm, 10 μm, and 5 μm.

6. The multi-layer detector according to claim 1, wherein the detector pixel pitch of the first sensor and/or of the second sensor in a second direction is less than or equal to 200 μm.

7. The multi-layer detector according to claim 6, wherein the detector pixel pitch of the first sensor and/or of the second sensor in the second direction is one of: 175 μm, 150 μm, 125 μm, 100 μm, 75 μm, 50 μm, 25 μm, 10 μm, and 5 μm.

8. The multi-layer detector according to claim 1, wherein the plurality of X-ray absorbing septa walls comprise at least one high-Z material.

9. The multi-layer detector according to claim 1, wherein the plurality of septa walls comprises a plurality of first septa walls substantially parallel to each other, and wherein a spacing between the first septa walls in a first direction is equal to an integer multiple n of detector pixel pitch of the first sensor and/or of the second sensor in the first direction, wherein n=2, 3, 4, . . . N.

* * * * *